(12) United States Patent
Leburton et al.

(10) Patent No.: US 8,702,929 B2
(45) Date of Patent: *Apr. 22, 2014

(54) SOLID STATE DEVICE

(75) Inventors: Jean-Pierre Leburton, Urbana, IL (US); Gregory Timp, Urbana, IL (US); Maria E. Gracheva, Potsdam, NY (US); Julien Vidal, Bages (FR)

(73) Assignee: The Board of Trustees of the University of Illinois, Urbana, IL (US)

( * ) Notice: Subject to any disclaimer, the term of this patent is extended or adjusted under 35 U.S.C. 154(b) by 83 days.

This patent is subject to a terminal disclaimer.

(21) Appl. No.: 13/427,442

(22) Filed: Mar. 22, 2012

(65) Prior Publication Data

US 2012/0175257 A1 Jul. 12, 2012

Related U.S. Application Data

(63) Continuation of application No. 12/237,551, filed on Sep. 25, 2008, now Pat. No. 8,192,600.

(60) Provisional application No. 60/975,774, filed on Sep. 27, 2007.

(51) Int. Cl.

| | |
|---|---|
| *C12M 1/00* | (2006.01) |
| *C12N 9/00* | (2006.01) |
| *C12N 11/00* | (2006.01) |
| *C25B 9/00* | (2006.01) |
| *C25B 11/00* | (2006.01) |
| *C25B 13/00* | (2006.01) |
| *G01N 1/00* | (2006.01) |
| *C02F 1/40* | (2006.01) |
| *C02F 11/00* | (2006.01) |
| *G01N 27/00* | (2006.01) |
| *G01F 1/64* | (2006.01) |
| *H01L 29/06* | (2006.01) |

(52) U.S. Cl.
USPC ......... 204/403.01; 204/600; 205/792; 257/30

(58) Field of Classification Search
USPC .......... 204/660, 600, 406, 416, 603; 205/792, 205/778
See application file for complete search history.

(56) References Cited

U.S. PATENT DOCUMENTS

| | | |
|---|---|---|
| 7,226,733 B2 | 6/2007 | Chan et al. |
| 7,258,838 B2 | 8/2007 | Li et al. |

(Continued)

FOREIGN PATENT DOCUMENTS

WO     WO 01/81896     11/2001

OTHER PUBLICATIONS

"Nanopore", Wikipedia, www.en.wikipedia.org/wiki/Nanopore, Sep. 23, 2008, 2 pages.

(Continued)

*Primary Examiner* — Luan Van
*Assistant Examiner* — Louis Rufo
(74) *Attorney, Agent, or Firm* — Guntin & Gust, PLC; Ed Guntin

(57) ABSTRACT

A system that incorporates teachings of the present disclosure may include, for example, a solid-state selector having a vessel for carrying a liquid medium with one or more molecules surrounded by ions, a solid state conductive structure doped with impurities having one or more through-holes extending between two surfaces of the solid state conductive structure positioned within the liquid medium of the vessel, a voltage source coupled to the solid state conductive structure to selectively stimulate the ions surrounding the one or more molecules to pass through the one or more through-holes. Additional embodiments are disclosed.

17 Claims, 16 Drawing Sheets

(56) References Cited

U.S. PATENT DOCUMENTS

| | | |
|---|---|---|
| 8,192,600 B2 * | 6/2012 | Leburton et al. ......... 204/403.01 |
| 2003/0116531 A1 | 6/2003 | Kamins et al. |
| 2005/0227239 A1 | 10/2005 | Joyce |
| 2006/0243655 A1 | 11/2006 | Striemer et al. |
| 2006/0276047 A1 | 12/2006 | Ouyang et al. |
| 2007/0042366 A1 | 2/2007 | Ling |
| 2007/0134840 A1 | 6/2007 | Gadeken et al. |

OTHER PUBLICATIONS

"Solid-State Nanopores for Gene Sequencing", Ames Technology Capabilities and Facilities, http://2www.nasa.gov/centers/ames/research/technology-onepagers/nanopores_gene_sequen . . . , Sep. 23, 2008, 1 page.

Daiguji, et al., "Nanofluidic Diode and Bipolar Transistor", NanoLetters, vol. 5, No. 11, 2005, 2274-2280.

Dimitrov, et al., "Exploring the Prospects for a Nanometer-Scale Gene Chip", IEDM Tech. Digest, 2006, 169-173.

Doyle, et al., "The Structure of Potassium Channel: Molecular Basis of K+ Conduction and Selectivity", Science, 1998, 69-77.

Fan, et al., "DNA Translocation in Inorganic Nanotubes", NanoLetters, vol. 5, No. 9, 2005, 1633-1637.

Fologea, et al., "Slowing DNA Translocation in a Solid-State Nanopore", NanoLetters, vol. 5, No. 9, 2005, 1734-1737.

Gardner, et al., "Electrodiffusion model Simulation of Ionic Channels: 1 D Simulations", Journal of Computarional Electronics, 2004, 25-31.

Gracheva, et al., "Electrolytic Charge Inversion at the Liquid-Solid Interfacein a Nanopore in a Doped Semiconductor Membrane", Nanotechnology, 2007, 145704-145710.

Gracheva, et al., "Simulation of the Electric Response of DNA Translocation Through a Semiconductor Nanopore-Capacitor", Nanotechnology, 2006, 622-633.

Heng, et al., "Sizing DNA Using a Nanometer-Diameter Pore", Biophysical Journal, 2004, 2905-2911.

Heng, et al., "The Electromechanics of DNA in a Synthetic Nanopore", Biophysical Journal, vol. 90, 2006, 1098-1106.

Ho, C. et al., "Electrolytic transport through a synthetic nanometer-diameter pore", Proceedings of the National Academy of Sciences, vol. 102, No. 30, Jul. 26, 2005, 10445-10450.

Horiuchi, et al., "Electrokinetic Flow Control in Mircrofluidic Chips Using a Field-Effect Transistor", Lab. Chip 6, 2006, 714-723.

Karnik, et al., "Electrostatic Control of Ions and Molecules in Nanofluidic Transistors", A. Nanoletter, vol. 5, No. 5, 2005, 943-948.

Karnik, et al., "Rectification of Ionic Current in Nanofluidic Diode", NanoLetters, vol. 7 No. 3, 2007, 547-551.

Kasianowicz, et al., "Characterization of Individual Polynucleotide Molecules Using a Membrane Channel", Proc. Natl. Acad. Sci. USA, 1996, 1377013773.

Kralj, et al., "Continuous Dielectrophoretic Size-Based Particle Sorting", Anal. Chem., 2006, 5019-5025.

Li, et al., "Ion-Beam Sculpting at nanometre Length Scales", Nature, 2001, 166-169.

Li, Haibo et al., "Characterization and Modeling of a Microfluidic Dielectrophoresis Filter for Biological Species", Journal of Microelectromechanical Systems, vol. 14, No. 1, 2005, 103-112.

Li, Jiali et al., "DNA Molecules and Configurations in a Solid-State Nanopore Microscope", Nat. Mater, 2003, 611-615.

Nishizawa, et al., "Metal Nanotubule Membranes with Electrochemically Switchable ion-Transport Selectivity", C.R. Science, 1995, 700-702.

Ramirez, et al., "Synthetic Nanopores with Fixed Charges: An Electrodiffusion Model for Ionic Transport", Phys. Rev. E, 2003, 011910.

Siwy, et al., "Conicai-Nanotube ion-Current Rectifiers: The Role of Surface Change", J. Am. Chem. Soc., 2004, 10850-10851.

Siwy,, "ion-Current Rectification in Nanopores and Nanotubes with Broken Symmetry", Adv. Funct. Mater, 2006, 735-746.

Stein, et al., "Ion-Beam Sculpting Time Scales", Physical Review Letters,, vol. 89, No. 27, 2002, 276106-1.

Storm, et al., "Fabrication of Solid-State nanopores with Single-Nanometre Precision", Nat. Mater., 2003, 537-540.

Vlassiouk, et al., "Nanofluidic Diode", NanoLetters, vol. 7, No. 3, 2007, 552-556.

Zhou, et al., "Molecular Simulation of Aqueous Electrolytes in Model Silica nanochannels", Molecular Physics, vol. 101, No. 8, 2003, 1089-1094.

* cited by examiner

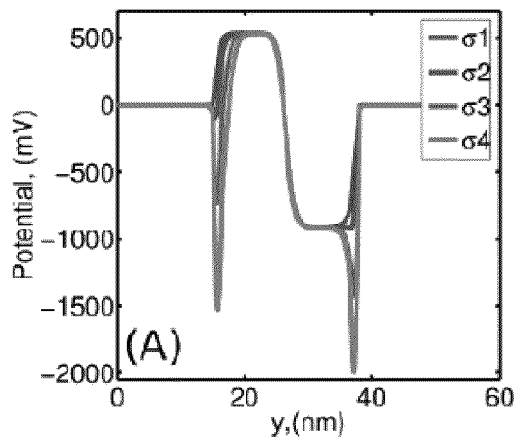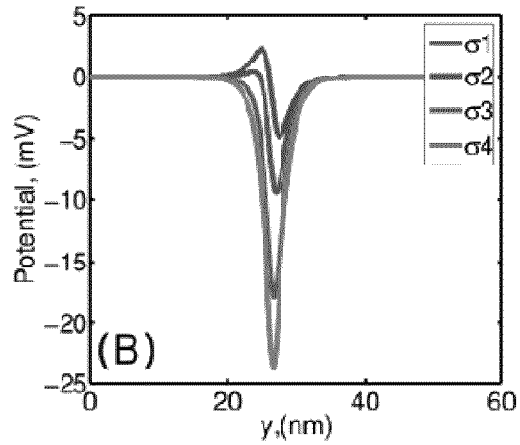
FIG. 2A  FIG. 2B
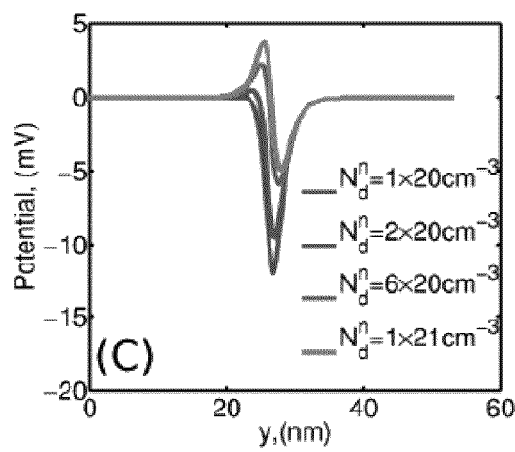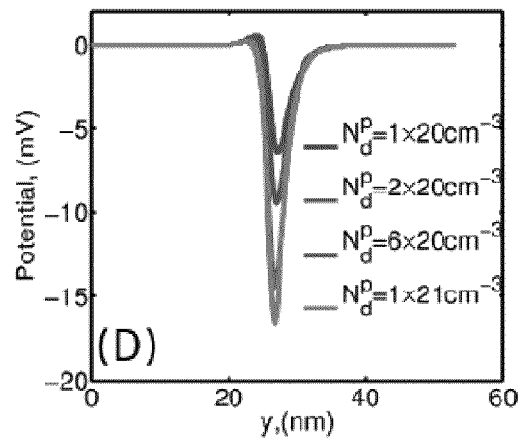
FIG. 2C  FIG. 2D

SOLID STATE DEVICE

CROSS REFERENCE

The present application is a continuation of U.S. application Ser. No. 12/237,551 filed Sep. 25, 2008, by Leburton et al., entitled "Solid State Device," which claims the benefit of priority to U.S. Provisional Application No. 60/975,774 filed on Sep. 27, 2007. All sections of the aforementioned applications are incorporated herein by reference in their entirety.

STATEMENT AS TO FEDERALLY SPONSORED RESEARCH

This invention was made with government support under CCR 02-10843 awarded by the National Science Foundation (NSF), and PHS1-R01-HG003713-01 awarded by the National Institutes of Health (NIH). The government has certain rights in this invention.

FIELD OF THE DISCLOSURE

The present disclosure relates generally to solid state devices.

BACKGROUND

Proteinaceous nanopores have been studied for the past decade for their essential role in biology as nanoscale channels regulating the ion flow through cell membranes as well as exhibiting ion selectivity. Properties of the track-etched membranes have been studied in comparison to the properties of the various biological channels. In the past few years, artificial nanopores in dielectric membranes etched by high-energy ion or electron beams [1,2] have been proposed as a substitute to biological ion channels [3-5]. However, such membranes are electrically insulating and do not provide tunable electrostatic control of the ion concentration inside or the ion flow through the nanopore. Recently, Karnik et al. [6] experimentally demonstrated the metallic gate-voltage modulation of ions and molecules concentration in a long channel with a nanoscale diameter to control the ionic conductance. Gold nanotubes with fully controlled ionic selectivity were reported in ref [7]. The ion selectivity was controlled by applying voltage to the tubes. Also, it was suggested that nanopores in $n^+$-Si membrane can be used as an ion filter by applying a voltage difference between the semiconductor and the electrolyte [8].

Similar to voltage-gated ion channels that belong to a class of transmembrane ion Channels activated by changes in the electrical potential difference near the channel, the presence of a surface charge in a solid-state membrane is central for the use of nanopores in single-molecule detection, ion/protein filtering [8], and potentially in DNA sequencing [9-11]. While the surface charge of biological channels can be positive, negative, or spatially distributed in the pore to operate the "gating" mechanism interrupting the flow of molecules, water or ions, the surface charge in solid-state nanopores is usually negative and results from the fabrication process [9]. In this context, conical nanopores in polymer membranes with various (negative) surface charges have been investigated as ion rectifiers [12]. Meanwhile, a microfluidic field effect transistor operating by surface charge modulation in an ion channel has been proposed [13], and theoretical modeling of ion transport in a nanofluidic diode and a bipolar transistor has been developed [14].

There is versatility in the use of semiconductor membranes in controlling the electrolyte charge in a nanopore [15]: unlike dielectric membranes that exhibit negative surface charges inducing positive ion charges at the nanopore surface, n-doped semiconductor membranes can attract either positive or negative ions at the nanopore surface depending on the amount of positive dopant charge in the depletion layer of the n-type semiconductor. Moreover, the semiconductor membrane can be connected to a voltage source to modulate the nanopore channel charge.

BRIEF DESCRIPTION OF THE DRAWINGS

FIG. 2A depicts an, illustrative embodiment of an electrostatic potential across the membrane along $S_2$ for difference surface charge densities $\sigma_1=0$, $\sigma_2=-0.256$ C/m$^2$, $\sigma_3=-0.076$ C/m$^2$ and $\sigma_4=-0.128$ C/m$^2$;

FIG. 2B depicts an illustrative embodiment of a potential in the nanopore along $S_1$ for the same charge densities as in FIG. 2A;

FIG. 2C depicts an illustrative embodiment of a potential in the nanopore along $S_1$ for different n-Si side doping densities $N_d^n$, with fixed doping density on the p-Si side of the membrane. $N_d^p=2\times10^{20}$ cm$^{-3}$ and surface charge density $\sigma_2$;

FIG. 2D depicts an illustrative embodiment of a potential in the nanopore along $S_1$ for different p-Si side doping densities $N_d^p$, with $N_d^n=2\times10^{20}$ cm$^{-3}$ and $\sigma_2$. Solution concentration is [KCl]=1M in all cases;

FIGS. 7A-B are calculated for the electrostatic potentials presented in FIGS. 6A-F for the same system parameters;

FIG. 9A corresponds to anion and electron concentrations. FIG. 9B corresponds to cation and hole concentrations;

FIG. 11A for a surface charge of −0.064 Cm$^{−2}$, ion concentration of 1 M, FIG. 11B for a surface charge of −0.064 Cm$^{−2}$, a doping concentration $N_d^+$=5×10$^{20}$ cm$^{−3}$ and ion concentration of 1 M, FIG. 11C for a surface charge of −0.096 Cm$^{−2}$ and ion concentration of 1 M, FIG. 11D for a surface charge of −0.064 Cm$^{−2}$ and ion concentration of 0.1 M; FIG. 12A for a surface charge of −0.064 Cm$^{−2}$, an ion concentration of 1 M, FIG. 12 B for a surface charge of −0.064 Cm$^{−2}$, a doping concentration N; =5×10$^{20}$ cm$^{−3}$ and ion concentration of 1 M, FIG. 12 C for a surface charge of −0.096 Cm$^{−2}$ and ion concentration of 1 M, FIG. 12D for a surface charge of −0.064 Cm$^{−2}$ and ion concentration of 0.1 M.

DETAILED DESCRIPTION

One embodiment of the present disclosure entails a solid-state selector having a vessel for carrying a liquid medium with one or more molecules surrounded by ions, a solid state conductive structure doped with impurities having one or more through-holes extending between two surfaces of the solid state conductive structure positioned within the liquid medium of the vessel, and a voltage source coupled to the solid state conductive structure to selectively stimulate the ions surrounding the one or more molecules to pass through the one or more through-holes.

Another embodiment of the present disclosure entails a solid-state selector having a vessel for carrying a liquid medium with one or more molecules surrounded by ions, and a solid state conductive structure having a one or more through-holes extending between first and second surfaces of the solid state conductive structure positioned within the liquid medium of the vessel. The first surface can be doped with an n-type impurity, and the second surface can be doped with a p-type impurity. A first voltage source can be coupled to a first portion of the solid state conductive structure doped with the n-type impurity. A second voltage source can be coupled to a second portion of the solid state conductive structure doped with the p-type impurity. The first and second voltage sources can selectively stimulate the ions surrounding the one or more molecules to pass through the one or more through-holes.

Yet another embodiment of the present disclosure entails a solid-state device having a vessel for carrying a liquid medium with one or more molecules surrounded, a diode having one or more through-holes extending between first and second surfaces of the diode positioned within the liquid medium of the vessel, a first voltage source coupled to an anode terminal of the diode, and a second voltage source coupled to a cathode terminal of the diode. The first and second voltage sources can bias the diode to selectively stimulate the ions surrounding the one or more molecules to pass through the one or more through-holes.

Another embodiment of the present disclosure entails solid-state selector having a vessel for carrying a liquid medium with anions and cations, a solid state conductive structure doped with impurities having one or more through-holes extending between two surfaces of the solid state conductive structure positioned within the liquid medium of the vessel, a voltage source coupled to the solid state conductive structure to selectively stimulate the anions and cations to pass through the one or more through-holes.

Yet another embodiment of the present disclosure entails selectively stimulating one or more molecules to pass through one or more through-holes of a solid state conductive structure by applying a voltage to said structure.

Figure 1A:
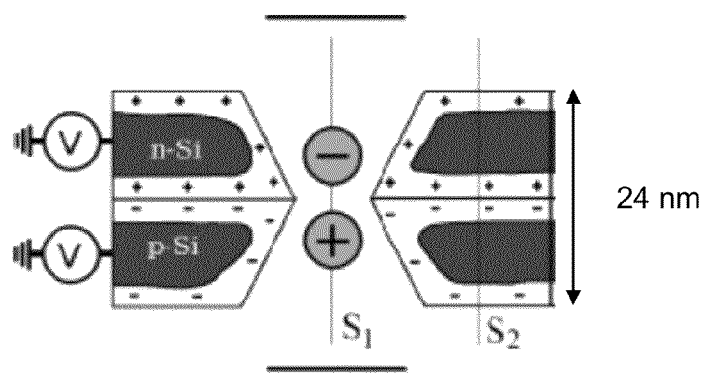
FIG. 1A depicts an illustrative embodiment of a geometry of the modeled nanopore in a solid-state membrane. The center X-Y cross-section is shown (the center Y-Z cross-section is similar). Two cuts $S_1$ and $S_2$ through the structure are indicated. $S_1$, is taken at the center of the nanopore, while $S_2$ is taken across the membrane, and is aligned with the pore axis. The drawing is not to scale.
Figure 1B:
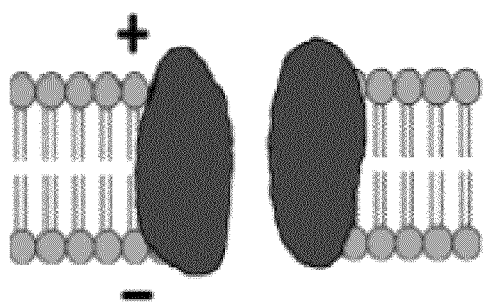
FIG. 1B depicts an illustrative embodiment of a biological channel in a polarized membrane.

Membrane Model. A nanopore-membrane structure geometry is shown schematically in FIGS. 1A-1B and consists of two 12 nm Si layers of different doping: the top layer is n-doped (typically $N_d^n$=2×10$^{20}$ cm$^{−3}$) and the bottom layer is p-doped (typically $N_d^p$=2×10$^{20}$ cm$^{−3}$). The nanopore in this solid-state membrane has a double-conical shape with a 1 nm diameter in the narrowest region and 6 nm diameter opening on each side of the pore as a result of the electron beam fabrication process, [9] but similar conclusions are expected for nanopores of more regular shape, e.g., cylindrical. The whole surface of the nanopore-membrane is covered by a 8 Å surface layer of SiO$_2$ containing a fixed negative charge σ. The surface charge density was varied at first, but unless otherwise indicated, the calculations are performed for σ=−0.0256 C/m$^2$. The membrane is immersed in an electrolyte KCl solution, with a concentration varying from 0.01M to 1M. Each material is characterized by its relative permittivity, i.e., $∈_{SiO}$=11.7, $∈_{SiO2}$=3.9. The dielectric constant of the electrolyte solution is chosen $∈_{electrolyte}$=78.

To obtain an ion charge distribution in the nanopore, the Poisson equation is solved self-consistently by a multigrid method in the electrolyte-membrane system, assuming the ions in the electrolyte are fully dissociated and obey the Boltzmann distribution, whereas electrons and holes in the semiconductor are governed by the Fermi-Dirac statistics. The model details are described in refs [3,15]. Virtual solid-state parameters can be used for a solution, which enables one to formulate an all-semiconductor model for the charge and electric potential in the electrolyte and solid-state materials [17]. The electrolyte/solid-state and semiconductor/oxide interfaces are modeled by introducing a conduction band offset between materials at their interfaces, i.e.: $E_c^{SiO2}$−$E_c^{Si}$=3.2 eV, $E_c^{solution}$−$E_c^{Si}$=−0.3 eV. The bias potential applied to the membrane is modeled with respect to the electrolyte by varying the quasi-Fermi levels of the Si n- ($V_n$) and p- ($V_p$) sides of the membrane separately over the −1 to 1 V range.

3D Electrostatic Potential. FIG. 2A shows a potential variation ("built-in" potential) inside the membrane along cross-section $S_2$ (FIG. 1A) for different densities of negative surface charges. No bias is applied to the membrane, so that there is no potential variation the electrolyte far from the membrane, which was set to 0 V for all studied electrolyte concentrations. The potential is positive on the n-side, and negative on the p-side of the membrane. Strong negative surface charges ($\sigma_3$ and $\sigma_4$) are manifested as two sharp drops in the potential profile at the top (y=16 nm) and the bottom (y=38 nm) surfaces of the membrane. FIG. 2B shows the potential variation in the nanopore along the pore axis ($S_1$, FIG. 1A) for different densities of negative surface charges. Here, the potential maximum decreases and the potential minimum deepens as the negative surface charge density increases. Thus, strong negative surface charges ($\sigma_3$ and $\sigma_4$) fully offset the positive dopant charge on the n-Si side of the membrane at considered doping density. The increase of the doping density on the n-side of the membrane boosts the potential maximum on the n-side, whereas the potential minimum on the p-side shrinks (FIG. 2C). The increase of the doping density on the p-side results in the potential minimum enhancement (FIG. 2D).

Parts C and D of FIG. 2 indicate that to obtain the maximum potential variation along the pore axis (condition that leads to the strongest current rectification), the doping density on both n-Si and p-Si sides of the membrane need to be maximized. Hence, the highest potential peak is achieved for the maximum doping density $N_d^n = 1 \times 10^{21}$ cm$^{-3}$ on the n-side (FIG. 2C), whereas, on the p-side, the deepest minimum is reached for the maximum doping density $N_d^p = 1 \times 10^{21}$ cm$^{-3}$ (FIG. 2D).

Figure 3A:
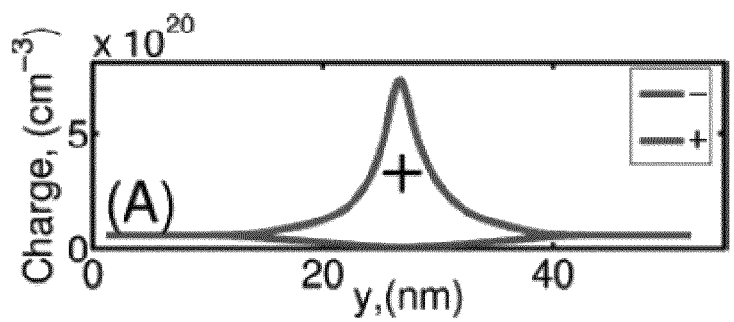
FIGS. 3A-B depict illustrative embodiments of an anion (CF) and cation (K$^+$) concentrations in the electrolyte solution in the nanopore center at $S_1$ of a p-n membrane for two membrane biases: (A) $V_n=-1$ V and $V_p=0$ V; and (B) $V_n=-1$ V and $V_p=0$ V. Simulation parameters: $\sigma=-0.0256$ C/m$^2$ $N_d^n=2\times10^{20}$ cm$^{-3}$, $N_d^p=2\times10^{20}$ cm$^{-3}$, [KCl]=0.1 M.
Figure 3B:
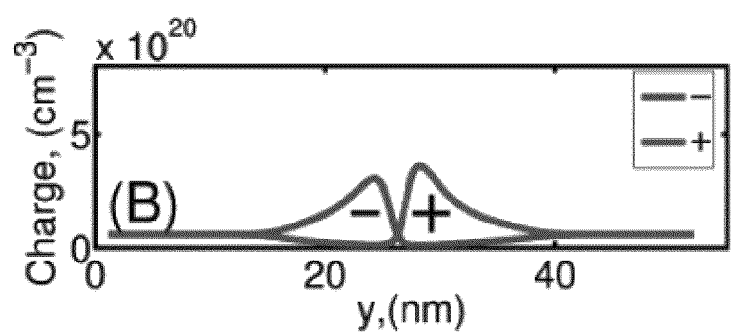

In FIGS. 3A-3B, anion and cation concentrations at the nanopore center are shown for a solution concentration [KCl]=0.1 M for two membrane biases. The first case (n-Si biased at $V_n = -1$ V, p-Si at $V_p = 0$ V, and electrolyte at V=0 V) is characterized by a single potential minimum in the pore, thus resulting in accumulation of cations in the nanopore center (FIG. 3A). The second case ($V_n = -1$ V, p-Si at $V_p = 0$ V, and electrolyte at V=0 V) gives rise to a potential profile with two extrema of opposite sign in the pore, which results in a dipolar ion charge in the pore: anions on the n-Si side and cations on the p-Si side of the membrane (FIG. 3B).

Figure 4A:
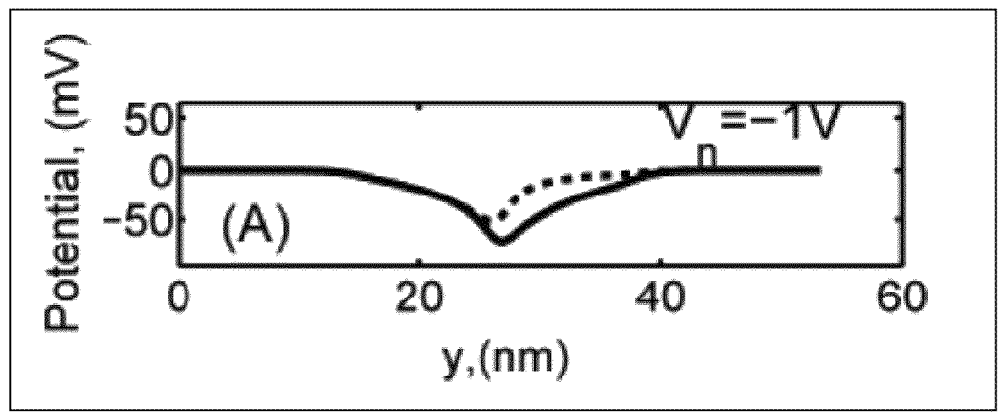
FIGS. 4A-D depict illustrative embodiments of an electrostatic potential in the nanopore along $S_1$ for [KCl]=0.1 M and surface charge density $\sigma=-0.0256$ C/m$^2$ for a p-n membrane (doping densities are $N_d^n=2\times10^{20}$ cm$^{-3}$ and $N_d^p=2\times10^{20}$ cm$^{-3}$), for all solid lines $V_p=-1$ V, for all dashed lines $V_p=1$V: (A) $V_n=-1$V (B) $V_n=0$V, and (C) $V_n=1$ V; (D) Electrostatic potential in the nanopore for a n-Si membrane, $N_d^n=2\times10^{20}$ cm$^{-3}$, all other parameters are as in the p-n membrane case, for various applied to the membrane potential biases.
Figure 4B:
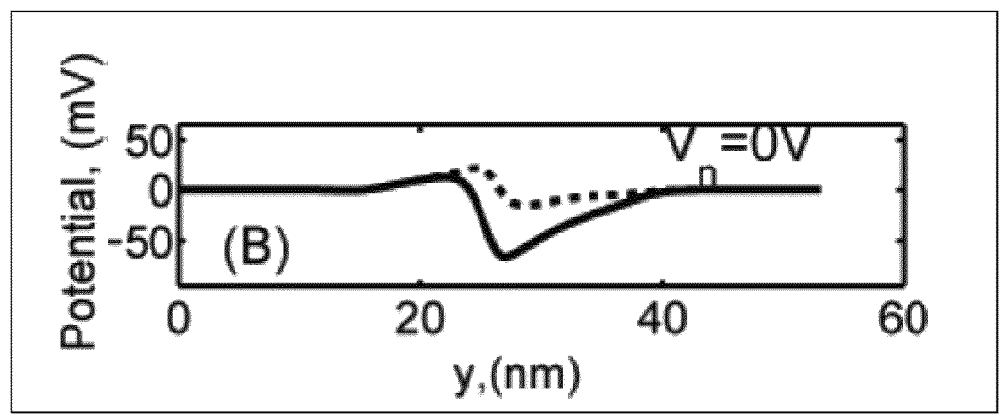
Figure 4C:
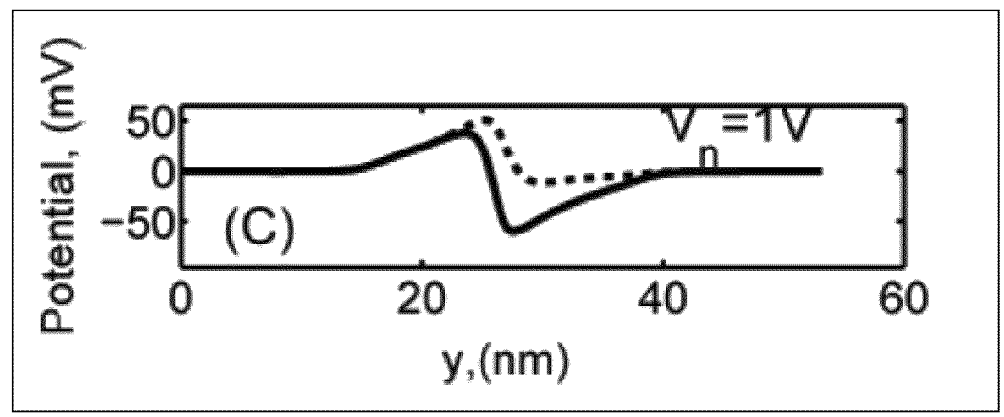
Figure 4D:
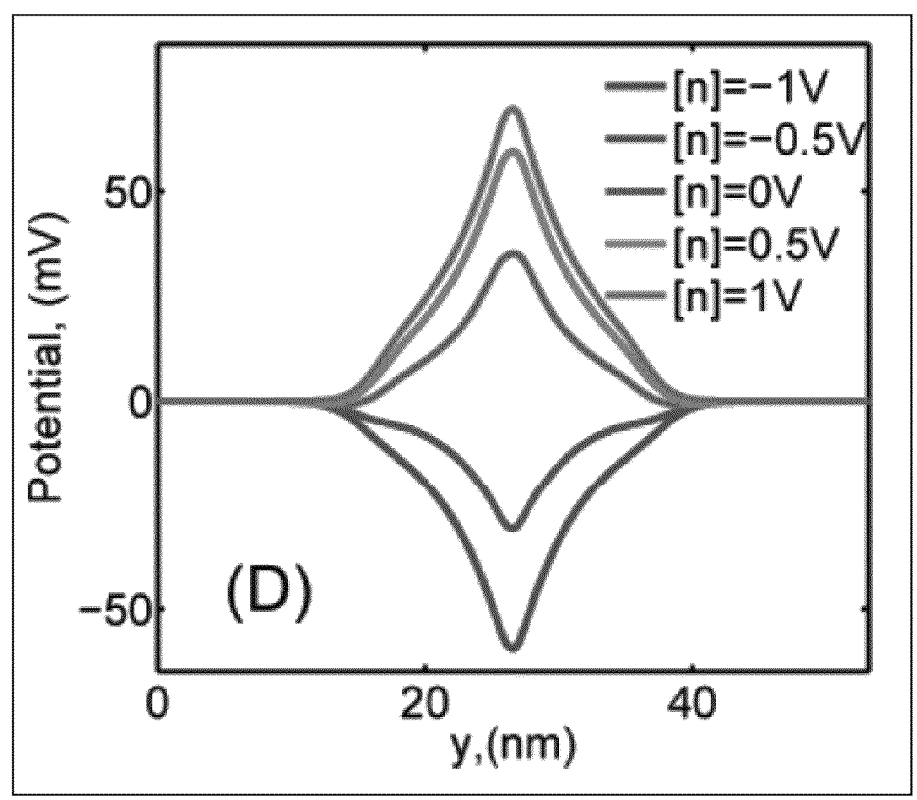

The potential profiles for a range of membrane biases are displayed in FIGS. 4A-C for a p-n membrane with typical material parameters and [KCl]=0.1M. For comparison, the potential profiles of a n-Si membrane with the same characteristics and a range of applied membrane biases are shown in FIG. 4D. Unlike the electrostatic potential profile of the n-Si membrane that exhibits a single potential extremum, i.e., either positive or negative, for all considered membrane biases, the potential along the channel in a p-n membrane produces either a single dominant maximum, a single dominant minimum, or two extrema (one minimum and one maximum) as a function of applied bias between the n- and p-layers. This specificity of the p-n membrane to produce asymmetric potential landscape in the channel is directly related to the ionic current rectification properties of the nanopores, as will be discussed in a later section.

Typical potential variations in the pore are ≥50 mV (FIGS. 4A-C), which is larger than the thermal voltage kT/e≅25 mV; one can expect larger variations at lower ion concentrations [KCl]<0.1M due to reduced screening of the nanopore walls by ions and, consequently, improved selectivity and rectification function.

Figure 5:
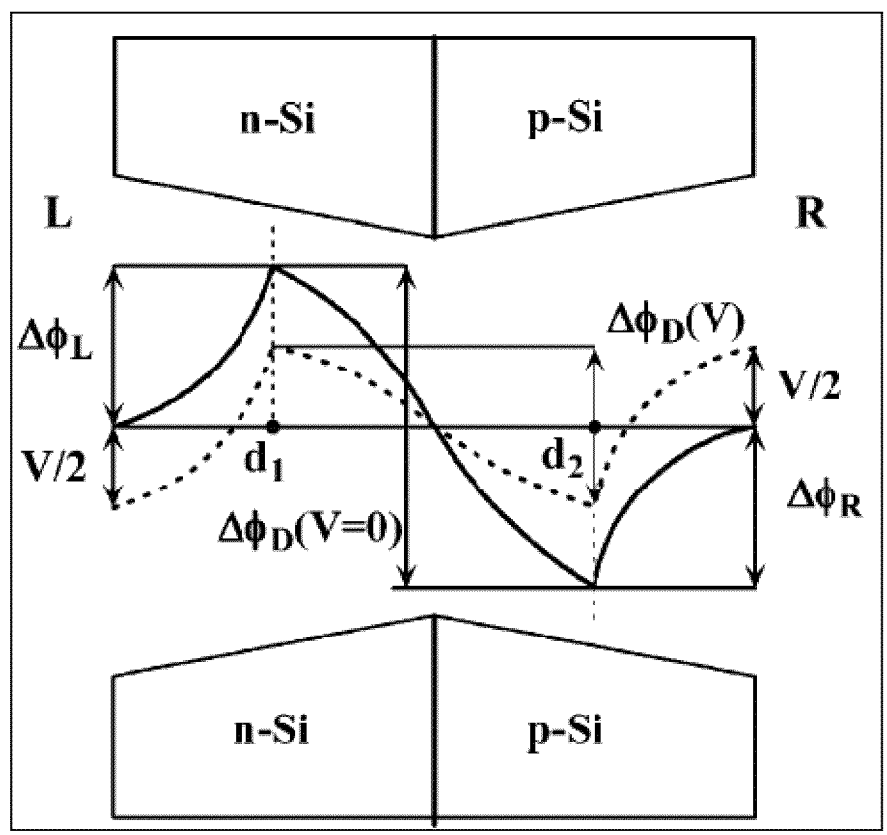
FIG. 5 depicts an illustrative embodiment of a sketch of the nanopore in a p-n membrane with one of the possible electrostatic potential variations in the nanopore. Positive current flows from the left to the right.

Current-Voltage Characteristics. To calculate the current-voltage characteristics of the electrolyte as a function of the potential landscape in the nanopore, an electrodiffusion model can be used for ionic transport similar to [18]. FIG. 5 shows a schematic profile of the potential with two extrema of opposite signs in the pore along the $S_1$ cross-section. The external and internal pore solution concentrations are connected through the following Donnan equilibrium conditions:

$$c_i(d_1) = c_{i,L} \exp\left(-\frac{z_i F}{RT}\Delta\phi_L\right) \quad (1)$$

$$c_i(d_2) = c_{i,R} \exp\left(-\frac{z_i F}{RT}\Delta\phi_R\right) \quad (2)$$

where $z_i$ is the charge number of species i. $C_{i,L}$ and $C_{i,R}$ denote species i concentration of electrolyte solution on the left and the right of the nanopore, correspondingly. Similar notation is used for the potential $\phi$: $\phi_L$ and $\phi_R$ are potentials on the left and on the right side of the membrane (they are equal when no driving bias is applied), whereas $\phi(d_1)$ and $\phi(d_2)$ are potentials at the coordinates x=$d_1$ and x=$d_2$ inside the pore, correspondingly. $\Delta\phi_L = \phi(d_1) - \phi_L$ and $\Delta\phi_R = \phi_R - \phi(d_2)$ are the Donnan potential drops through the left and right interfaces, respectively, and $\Delta\phi_D = \phi(d_2) - \phi(d_1)$ is the diffusion potential in the pore. The potential differences $\Delta\phi_L \Delta\phi_D$, and $\Delta\phi_R$ are determined directly from the calculated potential profiles in the nanopore.

The flux $J_i$ of species i through the nanopore can be described by the Nernst-Planck equations $$J_i = -D_i \frac{dc_i}{dx} - z_i D_i c_i \frac{F}{RT} \frac{d\phi}{dx} \quad (3)$$

where $D_i$ is the diffusion coefficient of species i in the pore solution, and constants F, R, and T have their usual meaning. The total electrical current I passing through the nanopore under the applied electrolyte bias V=$\phi_L - \phi R$ (see potential profile in FIG. 5 as dashed line between the two sides of the membrane) is given by $$I = F\pi r^2 \sum_i z_i J_i \quad (4)$$

and the bias potential difference applied to the system can be written $$V = -(\Delta\phi_L(V) + \Delta\phi_D(V) + \Delta\phi_R(V)) \quad (5)$$

Equations 3, 4, and 5 with boundary conditions (eqs 1,2) can be used to obtain analytical expressions of ionic fluxes when considering the constant field approximation between coordinates x=$d_1$ and x=$d_2$ $$J_i = \frac{z_i F}{RT} \frac{D_i \Delta\phi_D}{(d_2 - d_1)} \left[\frac{c_i(d_1)\exp(-z_i F \Delta\phi_D / RT) - c_i(d_2)}{1 - \exp(-z_i F \Delta\phi_D / RT)}\right] \quad (6)$$

By assuming that the potential drops $\Delta\phi_L$ and $\Delta\phi_R$ at the left and right interface do not change with applied bias, as in biological channels, the I-V characteristics can be obtained by substituting $\Delta\phi_D(V) = \Delta\phi_D(V=0) - V$ in the right-hand side of eq 6 with $c_{S,L} = c_{S,R} = C_0 = 0.01M$ on each side of the membrane; $D_K^+ = 1.95 \times 10^{-5}$ cm$^2$/s, $D_{Cl^-} = 2.03 \times 10$ cm$^2$/s can be used for the diffusion coefficients of potassium and chlorine ions, respectively. Once the total electrical current is calculated, the nanopore conductance $G=dI/dV$ and the ion selectivity $S=|(G_{Cl}-G_K)/(G_{Cl}+G_K)|$ in the nanopore are readily obtained.

Ion Current Rectification and Filtering. FIGS. 6A-F left column shows the electrostatic potential profiles in the nanopore for [KCl]=0.01M at different biases between the n-Si and p-Si sides of the semiconductor membrane at electrolyte bias V=0. The membrane potential biases $V_{n(p)}$ vary from $-1$ V to 1 V with respect to the electrolyte. For this low molar [KCl] concentration, the potential variations in the nanopore are dramatic, with up to 200 mV swing magnitude. The corresponding positive and negative charge distribution as well as current-voltage characteristics are shown in FIGS. 6A-F center and right columns, correspondingly. It is illustrated that, as a function of the voltage across the p-n membrane, the I-V characteristics behavior varies from quasi-ohmic (i.e., FIG. 6C right column with $V_n=-0.5$ V, $V_p=1$ V) to diode-like, with vanishing leakage current at V>0 (i.e., FIG. 6F right column with $V_n=1$ V, $V_p=0$ V)

Figure 6A:
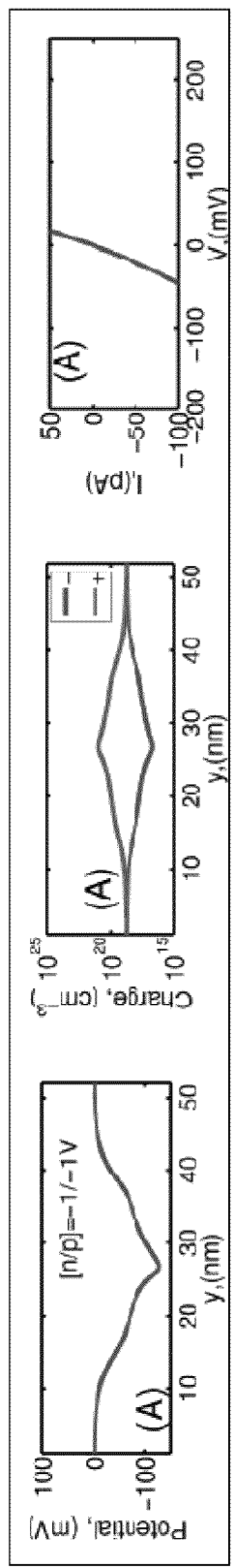
FIGS. 6A-F depict illustrative embodiments of an electrostatic potential in the nanopore along cross-section $S_1$ for various membrane biases. [KCl]=0.01 M and surface charge density $\sigma=-0.0256$ C/m$^2$ for p-n membrane (doping densities are $N_d^n=2\times10^{20}$ cm$^{-3}$ and $N_d^p=2\times10^{20}$ cm$^{-3}$). Electrolyte bias V=0. Membrane n- and p-layer bias potentials are indicated in legend as [n/p]. (Center, A-F) Positive and negative charge distributions in the nanopore along cross-section $S_1$ for the same p-n membrane biases. Note the log scale. (Right, A-F) Current-voltage characteristics calculated for the same, p-n membrane biases.
Figure 6B:
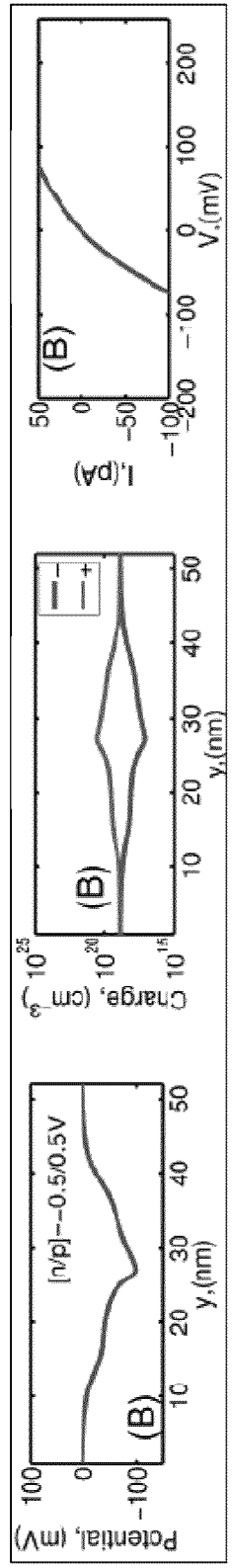
Figure 6C:
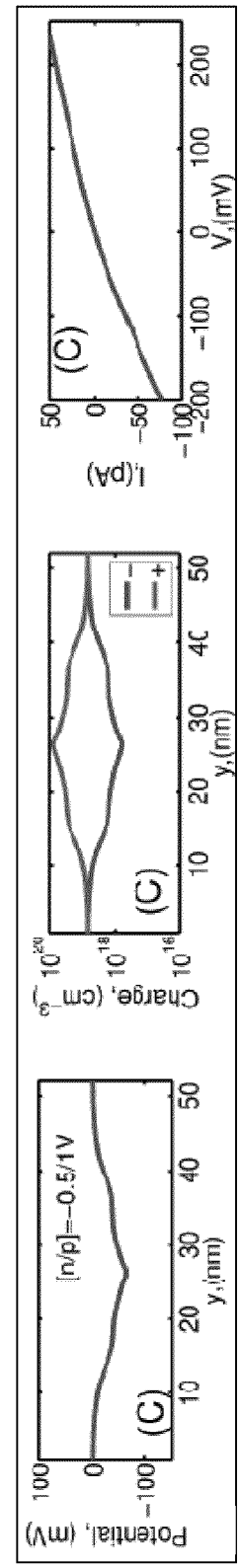
Figure 6D:
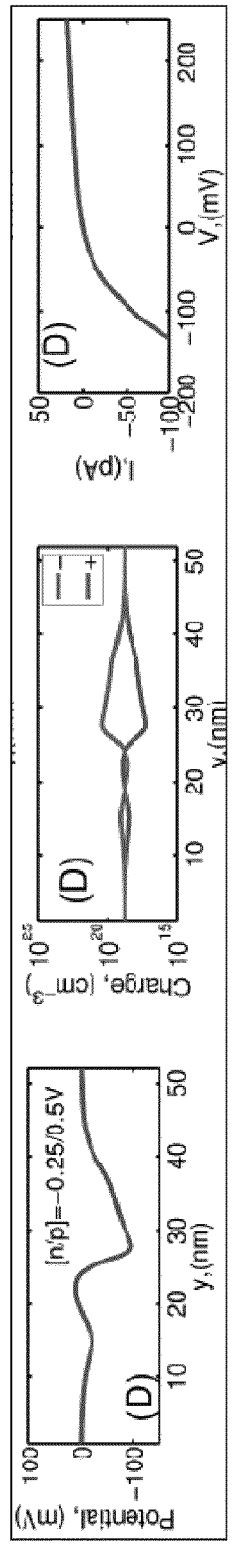
Figure 6E:
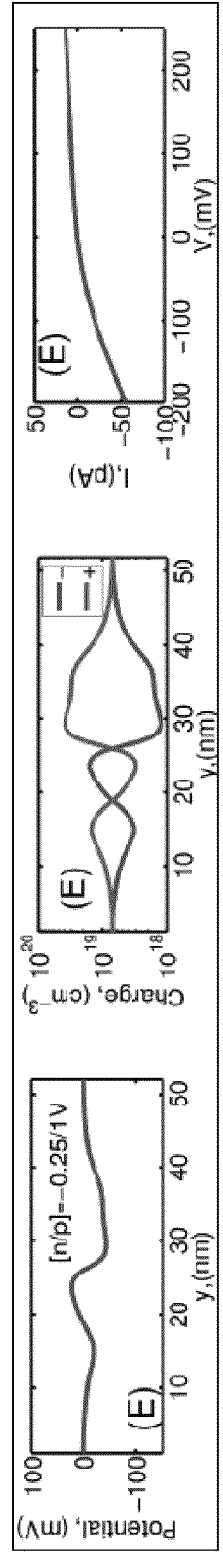
Figure 6F:
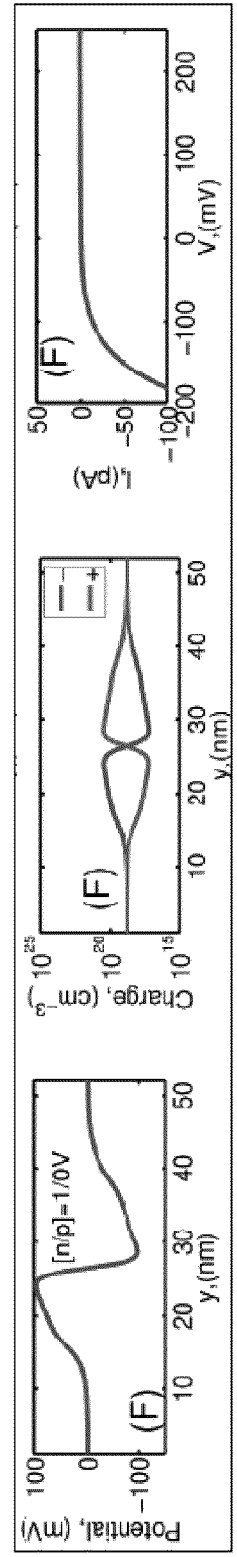

In this configuration, the ohmic behavior with the largest conductance is attributed to a potential profile with a single minimum of weak amplitude in the nanopore (FIG. 6C), while the sharpest diode-like characteristic corresponds to an anti-symmetric sine-like potential profile of large amplitude (FIG. 6F). All intermediate potential profiles result in asymmetric I-V characteristics for which the conductance at V<0 is always larger than the conductance at positive electrolyte bias V>0. The closer the potential profile to a sine-like shape, the better the rectification. The lower the potential amplitude, the closer the ohmic behavior. Correspondingly, the more symmetric the charge distribution with respect to the nanopore center, the "more ohmic" the current (FIGS. 6A-6C). Alternatively, the more asymmetric the charge distribution, the more rectified the current (FIG. 6D-6F). The fact that the high conductance regime is at negative electrolyte bias is due to the p-n membrane configuration for which the n-layer is on the same side as the positive solution electrode.

Figure 7A:
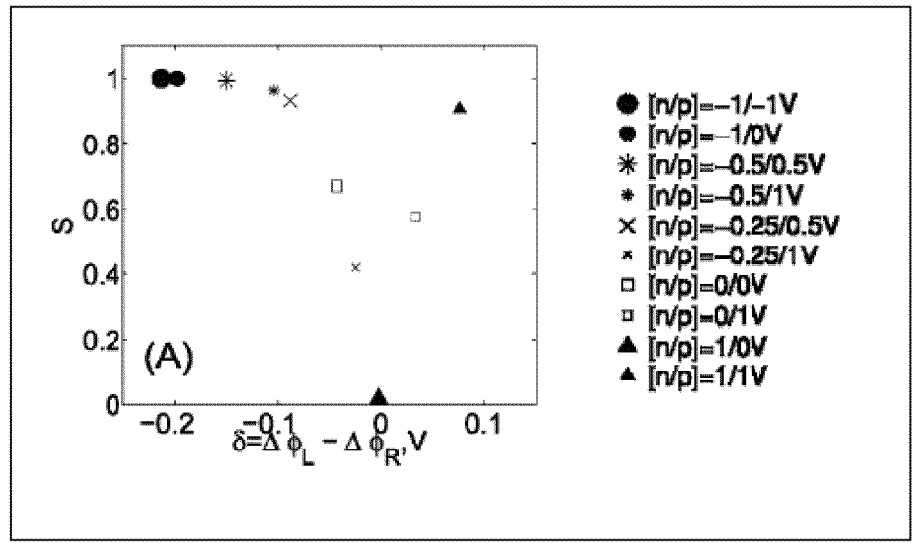
FIG. 7A depicts an illustrative embodiment of an ion selectivity.
Figure 7B:
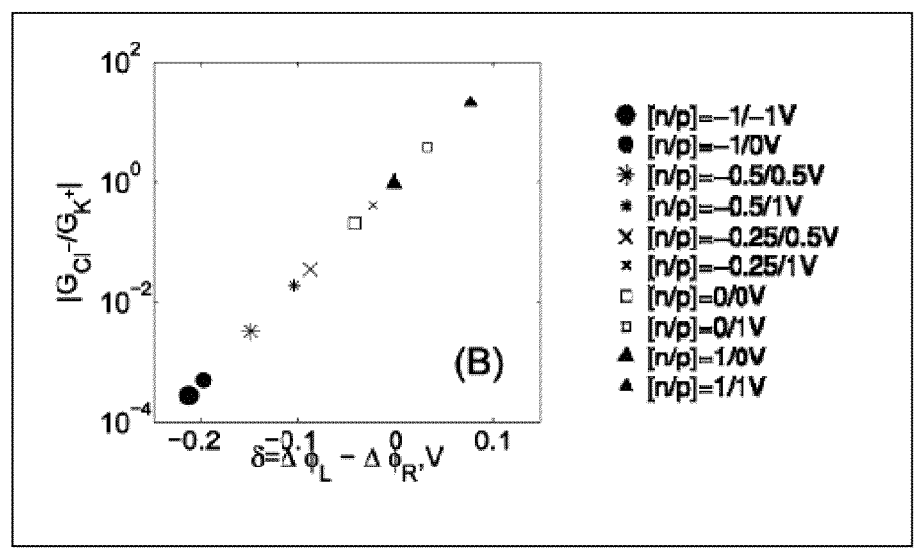
FIG. 7B depicts an illustrative embodiment of an ion conductance ratio.

FIG. 7A plots the selectivity S of the nanopore as a function of $\delta=\Delta\phi_L-\Delta\phi_R$ at different membrane p- and n-layer biases. It can be observed that the selectivity $S\approx 0$ when $\delta\approx 0$, which corresponds to an anti-symmetric (sine-like) shape potential (rectification condition) (FIG. 5), whereas the selectivity increases with the absolute value of 5 and even reaches $S\approx 1$ for $\delta=-200$ mV (conditions far from rectification). FIG. 7B shows the relative ionic conductance $G_{Cl}/G_K$ plotted in log scale as a function of $\delta$. It can be seen that the relative conductance increases exponentially with $\delta$, which is consistent with the flux expression (eq 6). The low selectivity regime with $\delta\approx 0$ corresponds to a relative conductance close to unity. The left-hand sides of both FIGS. 7A-7B with $\delta<0$ correspond to high selectivity and high conductance for positive $K^+$ ions because $G_{Cl}/G_K<<0$, while the right-hand sides of the FIGS. 7A-7B plots with $\delta>0$ correspond to high selectivity and high conductance for negative Cl_ ions because $G_{Cl}/G_K>>0$.

The membranes under biases that result in nanopore potentials with double extrema of equal height lead to the low selectivity regime (i.e., $V_n=1$ V, $V_p=0$ V). Alternatively, the nanopore potentials with a single extrema result in the high selectivity regime, with a single potential minimum being selective toward positive ($K^+$) ions (i.e., $V_n=-1$ V, $V_p=-1$ V), whereas a large potential maximum is being selective toward negative ($Cl^-$) ions (i.e., $V_n=1$ V, $V_p=1$ V).

Accordingly, current rectification and filtering are two different regimes corresponding to two different charge states of the p-n membrane, which can be tuned by electrically biasing the p-n layers. More generally, the p-n membrane can be used for separation of charged species, controlled injection, release, and blockade of charged molecules and ions, thereby minimizing in a very basic way the operation of voltage gated biological channels in cells. The p-n nanopore device also provides an opportunity to trap, stretch; and effectively slow down DNA translocation in the pore, thus rising the resolution of the proposed nanopore sequencing device [3,4].

It is known that a biological channel in a cell membrane can be electrically asymmetric with respect to the membrane plane to perform some form of selectivity or rectification. Similarly, an artificial nanopore with asymmetric electrical potential profile (whether it comes from asymmetry in pore geometry, surface charge distribution, or both) in a nanopore can produce ion current rectification through the pore with applied electrolyte bias. In the present disclosure it has been shown that unlike conical nanopores with predefined rectifying properties [12,19], nanopores in a p-n membrane can be tuned electrically from ohmic behavior to any desirable rectification and to a complete blockade of the total ionic current without the need for buffer solution replacement or membrane treatment. Simultaneously it can perform as an ion filter with the possibility of filtering ions of either sign.

Vlassiouk and Siwy and Karnik et al. [20,21] discuss the use of single nanopores decorated with fixed local positive charges as a nanofluidic "diode" and ion current rectifier. While these configurations provide rectification, additional flexibility can be obtained via manipulation of the solution pH once the surface charge is deposited or via chemical modification of the membrane to invert the I-V curves.

From the foregoing descriptions, it would be evident to an artisan with ordinary skill in the art that the aforementioned embodiments can be modified, reduced, or enhanced without departing from the scope and spirit of the claims described below. For example, in another illustrative embodiment a Si-membrane can contain a nanopore immersed in an electrolytic transport bi-cell. The cells on each side of the membrane can contain a volume of KCl electrolyte and an electrode positioned at 1 mm from the membrane.

Figure 8:
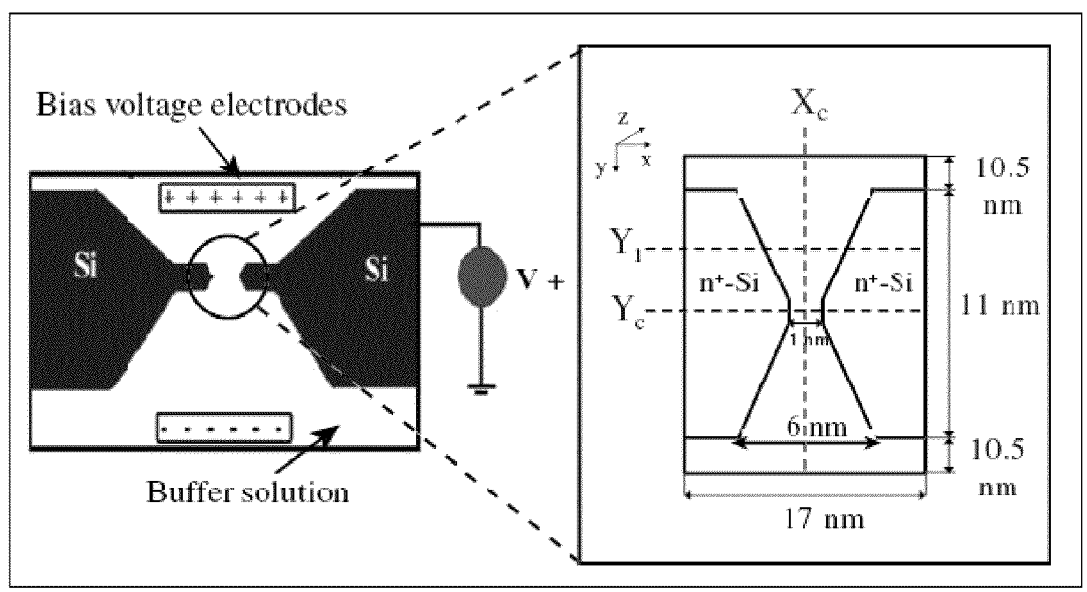
FIG. 8 depicts an illustrative embodiment of a schematic of the device geometry: xy cross-section through the center of the device. The drawing is not to scale.

FIG. 8 illustrates schematically the solid-state nanopore device where a potential difference between the electrodes in each cell drives the ion current through the nanopore. The solid-state membrane is very thin (7=10 nm) and made of heavily doped polysilicon. A nanopore of diameter smaller or equal to 2 nm is etched through the membrane using a tightly focused, high-energy electron beam to sputter atoms [26]. As a consequence, the nanopore has the shape of two inverted cones. The principle of operation is simple: by applying a positive (negative) potential difference between the polysilicon and the electrolyte, negative (positive) ions are attracted into the nanopore and positive (negative) ions are repelled and thereby modulating selectively the conductance of the respective ions.

3D Self-consistent Model

A simulation volume can be defined by focusing on the pore region which is the active region of the device for which a schematic cross-section of the idealized device is shown on FIG. 8. Several specific coordinates can be denoted MN, for which the mobility profiles are displayed in subsequent figures. The system can consist of a thin layer of heavily doped $n^+$-Si with a doping concentration $N_d^+=2\times 10^{20}$ $cm^3$ surrounded by a thin 2 Å layer of negative charge with volume density $N_{surface}=2\times 10^{21}$ $cm^{-3}$ as a result of the etching process. The electrolyte charge can originate from $K_+$ and $Cl^-$ ions. At room temperature the molecules can be fully ionized. Recently, Eisenberg et al. investigating transport in ion channels using semiconductor device formalism showed that their treatment is fully reliable to account for experimental results.

In the present disclosure, the electrolyte can be considered as a continuum and the semiconductor equation formalism can be used to model its electrical properties as well as those of the silicon membrane. Hence, the system consists of two material regions defined by their relative permittivity, i.e., $\epsilon_{Si}=11.7$ for the Si-membrane and $\epsilon_{solution}=78$ for the solution. Although the local permittivity can vary from 78 to 1 depending whether the water is totally excluded or not of the nanopore in this analysis, any spatial variation of $\epsilon_{solution}$ can be neglected. In this framework, the KCl solution is assumed to be an intrinsic semiconductor. In the presence of an electrostatic potential $\phi(r)$, the ion concentrations [Cl$^-$] (r) and [K$^+$] (r) obey Boltzmann Statistics:

$$[K^+](r) = [K^+]_0 \exp\left[\frac{q\phi(r)}{k_B T}\right] \tag{1}$$

$$[Cl^-](r) = [Cl^-]_0 \exp\left[-\frac{q\phi(r)}{k_B T}\right]. \tag{2}$$

where [K$^+$]$_0$ and [Cl$^-$]$_0$ are the equilibrium concentrations, T the temperature and $k_B$ the Boltzmann constant. The net ionic charge density in the solution is:

$$\rho_{solution} = q\{[K^+](r) - [Cl^-](r)\} \tag{3}$$

In the Si-layer, the carriers are degenerate, and their distributions follow the Fermi-Dirac distribution. The local density of charges in the semiconductor region is given by:

$$\rho_{solid\text{-}state}(r) = q(r)\{N_d^+(r) - N_s^-(r) + p(r) - n(r)\}, \tag{4}$$

where $N_d^+$ is the fully ionized donor density and $N_s^-$ is the fixed surface charge. Poisson's equation, $$\vec{\nabla} \cdot (\epsilon(r) \vec{\nabla} \phi(r)) = -\rho(r), \tag{5}$$

is solved self-consistently by a multigrid approach on the whole device under investigation. The grid spacing ranges from 4 Å to 0.5 Å as to be less than the Debye length. Dirichlet boundary conditions can be assumed on top and bottom bias gate region and Neumann boundary condition elsewhere. With no applied voltage, Fermi level in the whole device are set to zero, but when a voltage $V_{SE}$ is applied between the semiconductor and the electrolyte, their respective quasi-fermi levels $E_{f\,silicon}$ and $E_{f\,electrolyte}$ are split according to:

$$E_{f\,silicon} - E_{f\,electrolyte} = -qV_{SE}. \tag{6}$$

Figure 9A:
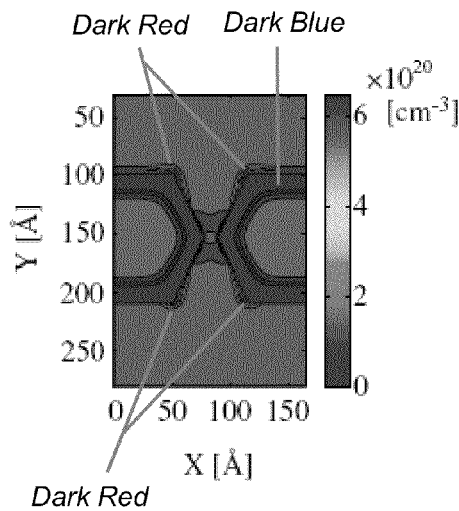
FIGS. 9A-B depict illustrative embodiments of a contour plot of ion concentration in the electrolyte and mobile charges in the membrane for a surface charge of −0.064 C m$^{−2}$, a doping concentration $N_d^+$=2×10$^{20}$ cm$^{−3}$ and an ion concentration, of 1 M.
Figure 9B:
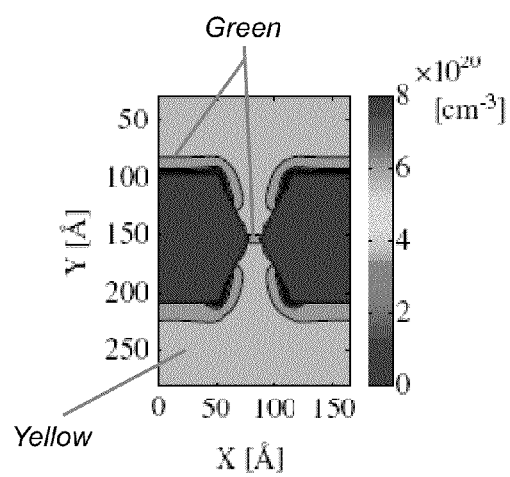
Figure 9C:
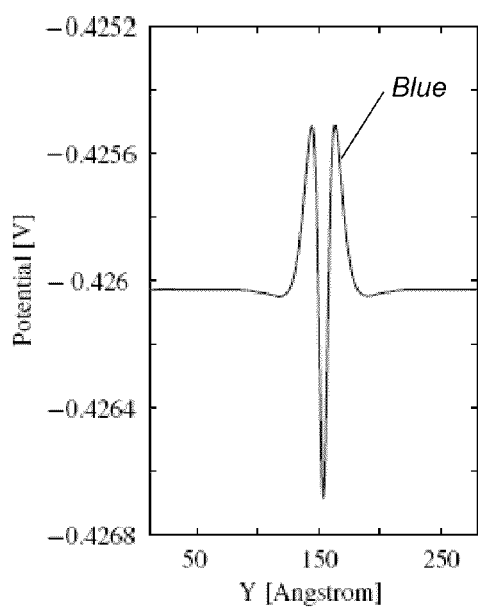
FIGS. 9C-D depict illustrative embodiments of a potential profile at $X_c$ along the Y-direction and at Y, (FIG. 9D red curve) and $Y_1$ (FIG. 9D blue curve) along the X-direction.
Figure 9D:
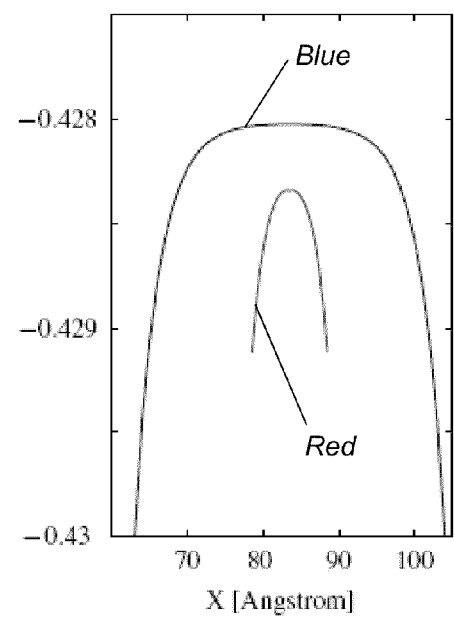

FIGS. 9A and 9B display both cation and anion concentrations for $V_0 = V_{SE} = 0$. FIGS. 9C and 9D show the corresponding potential profiles along respectively $Y_c$ (red curve) and $Y_1$ (blue curve). On FIG. 9A, it can be observed that the depletion layer (positive $N_D^+$ charge, dark blue of FIG. 9A) in the n$^+$-region running along the semiconductor membrane, which inverts the ionic population (Cl$^-$ dominant) along the slanted part of the nanopore (dark red in FIG. 9A and green in FIG. 9B). At the tip and the wide opening of the pore, cations are attracted close to the semiconductor surface due to the negative surface charge (dark red in FIG. 9A), while anions are strongly repelled (green and yellow in FIG. 9B). The potential variation along the Y-direction is relatively weak because of the strong screening provided by the high ion concentration. It is sufficient, however to distinguish inhomogeneous anion and cation distributions in the nanopore. On FIG. 9C the potential minimum at the pore center followed by two maxima is due to the particular double conic shape of the pore. On FIG. 9D the smaller variation is at $Y_c$, in the pore constriction, as expected.

Recent experimental data indicate the ion conductance decreases with pore radii due to the surface roughness, which implies ion mobilities vary spatially inside the nanopore. A phenomeno-logical model can be used for the mobility of each type of ions to ensure it vanishes on the nanopore wall i.e., $$\mu_{a,c}(r) = \mu_{a0,c0}\left\{1 - \exp\left[\frac{-|r - R(y)|^{\gamma_{a,c}}}{\delta_{a,c}^{\gamma_{a,c}}}\right]\right\}, \tag{7}$$

Figure 10A:
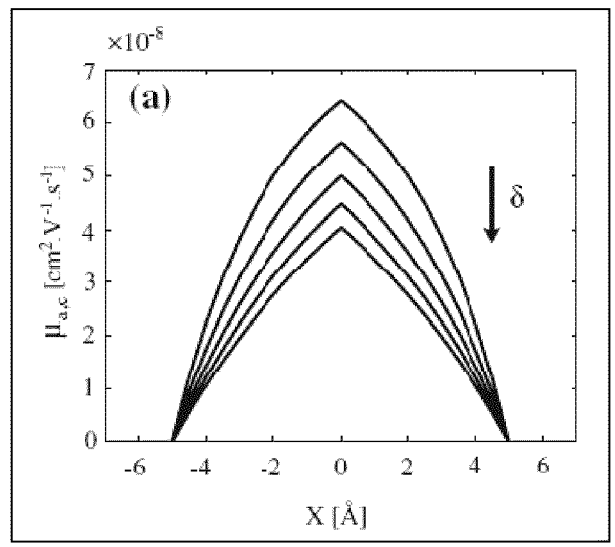
FIGS. 10A-B depict illustrative embodiments of mobility profiles at different positions in the channel: (a) along the center plane of the device $Y_c$ for different δ varying by unitary step from δ=3 Å to δ=7 Å and γ=1 (b) along $Y_1$ near the wall for γ varying by unitary step from γ=1 to γ=5 and δ=5.

Here, the subscripts a and c refer to anions and cations, respectively, $\mu_{a0,c0}$ is the ionic bulk mobility, r is the radial distance from the center of the pore, R(y) is the pore radius at ordinate y, $\delta$ and $\gamma$ are two fitting parameters that account for the decay of the mobility near the pore wall. It can be assumed that $\delta$ and $\gamma$ are the same for both Cl$^-$ and K$^+$ because the bulk mobility for cations and anions is practically the same i.e., $\mu_{a0}=7.91\times10^{-8}$ m$^2$V$^{-1}$s$^{-1}$, $\mu_{c0}=7.12\times10^{-8}$ m$^2$V$^{-1}$s$^{-1}$ Specifically:

$\delta$ is a characteristic length that accounts for the reduction of ion mobility due to the presence of the solid-state surface in the nanopore. Hence, for r=0 and R=5 Å, if we choose $\gamma=4$ and $\delta=8$ Å, $$\mu_{a,c} \approx \mu_{a0,c0}\left(\frac{R}{\delta}\right)^{\gamma}$$

and the mobility is reduced by 85% compared with the bulk values, which is consistent with existing data [27]. FIG. 10A displays the mobility profile along the $y_7$ direction (FIG. 8) in the narrowest region of the device as 6 is varied. It is seen that as $\delta$ increases $\mu_{a,c}$ (r=0) decreases.

Figure 10B:
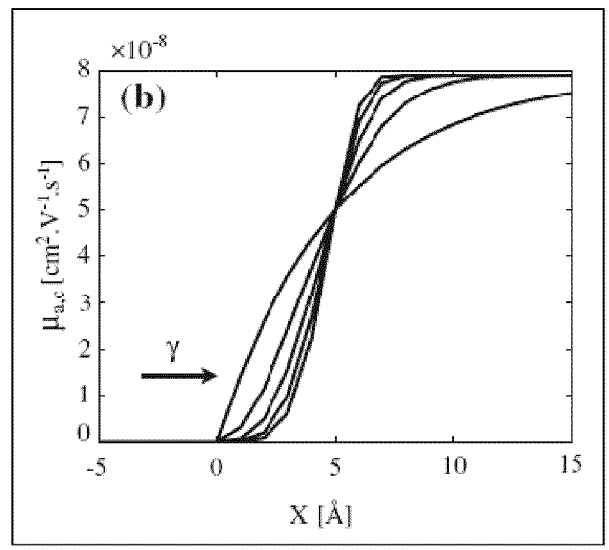

$\gamma$ accounts for the rate of decrease of the counterion mobility near the surface. Hence, for $|r-R|=\epsilon \approx 0$, $$-\frac{d\mu_{a,c}}{d_r} \propto \epsilon^{2\gamma-1}$$

and $\mu_{a,c} \propto \epsilon^\gamma$. FIG. 10B shows the mobility profile along the $\gamma_1$ direction (FIG. 8) for different values of $\gamma$. It is seen that the mobility variation is smoother in the vicinity surface as $\gamma$ increases (i.e., $$\frac{d\mu_{a,c}}{d_r}$$

is small).

The potential variation can be modeled through the nanopore with the following analytical expression, which has been shown to be valid from molecular dynamics in nanopore [28]:

$$V(y) = \frac{V_0}{\pi}\tan^{-1}(y/L_{eff}), \tag{8}$$

where $V_0$ is the external voltage across the device driving the ions through the nanopore and $L_{eff}$ is a characteristic length (not the channel length) so that the potential achieves its electrode values at $y=[-L_y/2, L_y/2]$ where $L_y$ is the channel length, with non-zero electric field at the electrodes. An approximation can be made that reservoir resistance is negligible in comparison with nanopore resistance and the potential in the reservoir is mostly constant.

Considering both anion density current and cation density current and neglecting the diffusion current, the current density for each ion type is given by:

$$J_a = q\mu_a a \nabla \phi \qquad (9)$$

$$J_c = q\mu_c c \nabla \phi \qquad (10)$$

$$J = J_a + J_c \qquad (11)$$

where $\mu_a$ and $\mu_c$ are the anion and cation mobility, respectively. Assuming no recombination inside the pore, it follows that $$\nabla J_{a,c} = 0, \qquad (12)$$

which by using the divergence theorem, implies that the current is constant through the nanopore. Due to the one dimensional nature of the external potential (8), this condition (12) is not fully satisfied [22]. The current can be spatially average through the nanopore to eliminate the slight J-variations due to the slanted geometry of the nanopore:

$$\langle I_{a,c} \rangle = \frac{1}{L} \int_{L/2}^{-L/2} dy \int \int_{S(y)} J_{a,c}(r) dS, \qquad (13)$$

Here L is the length of the pore and S(y) is the nanopore cross section at ordinate y. In this context, each ion conductance in the nanopore can be defined as $$G_{a,c} = \langle I_{a,c} \rangle / V_o. \qquad (14)$$

At zero electrolyte-membrane bias $V_{SE}$, there is predominance of cations inside the pore due to the presence of the negative charge on the nanopore wall irrespectively of the pore size and electrolyte concentration. When varying $V_{SE}$, the ion concentration inside the pore changes according to the voltage magnitude and its polarity. FIGS. 11A-D show the average volumic concentrations for both $K_+$ and $Cl_-$ ions defined as $$n_{avg} = \frac{\int\int\int n(r)dr}{V_{pore}}, \qquad (15)$$

for various pore shapes, surface charges on the semiconductor and electrolyte concentrations as functions of $V_{SE}$ at $V_0=0$. Here $V_{pore}$ is the volume of water inside the pore and n(r) the ion concentration at position r. Equation 15 directly provides the number of ions inside the pore since $V_{pore}$ is only dependent on the nanopore geometry. The cation concentration gain can be denoted as $$\beta_c^+ = \frac{[K^+]}{[Cl^-]}$$

and the cation conductance gain as $$\beta_G^+ = \frac{G_c}{G_a}$$

Figure 11A:
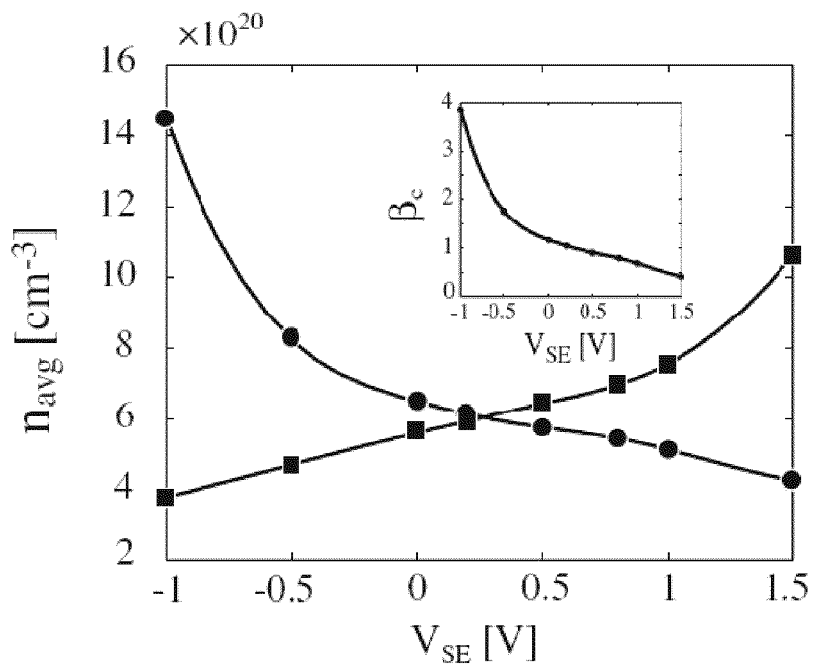
FIGS. 11A-D depict illustrative embodiments of an average volumic concentration of K$^+$ (circle) and Cl$^−$ (square) and insets: $β_c$, versus voltage applied.
Figure 11B:
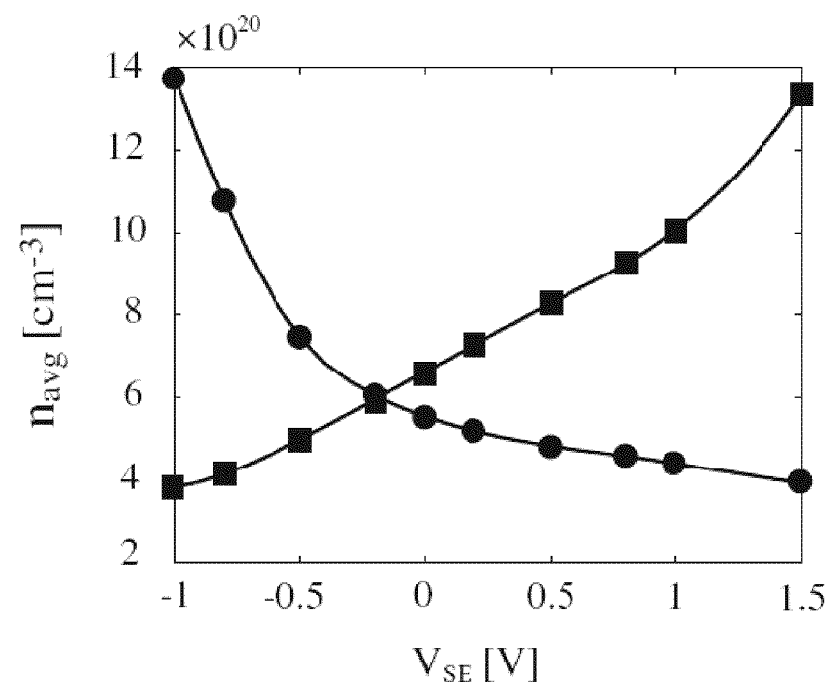
Figure 11C:
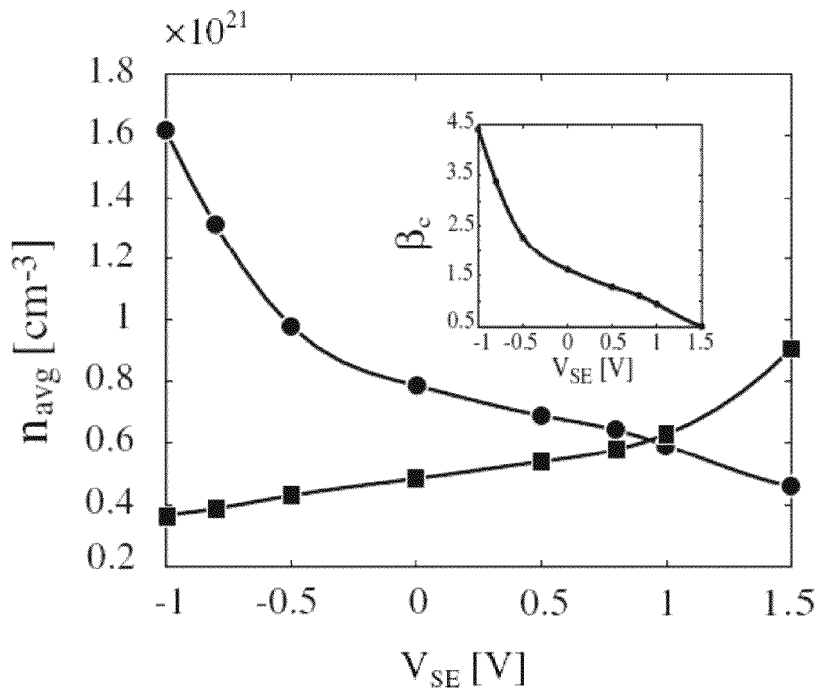
Figure 11D:
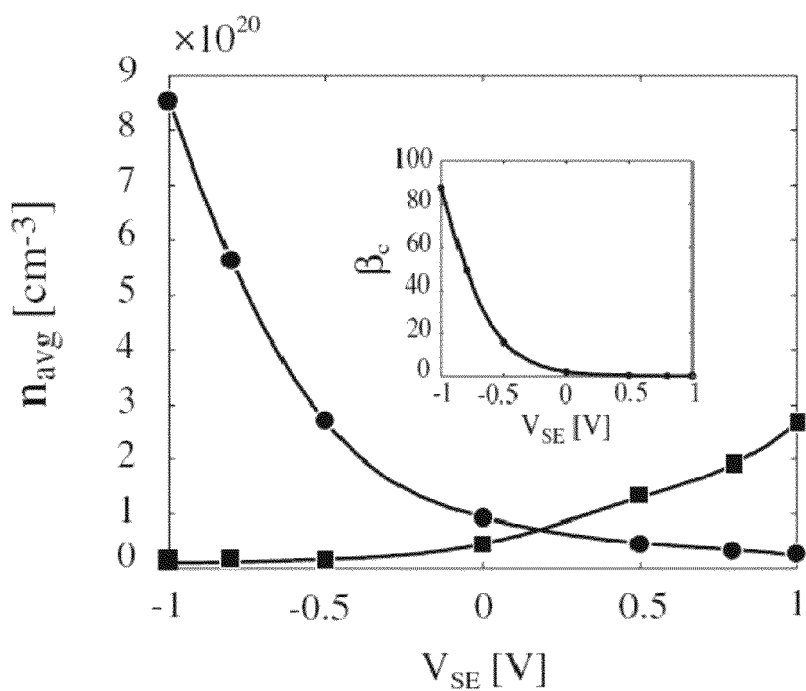

(The corresponding anion gains are the inverse of these quantities). For all four cases, the respective ion concentrations change monotonically with applied voltage. Hence, when the voltage $V_{SE}$ is sufficiently negative, cations are predominant in the nanopore, while at high positive voltages, the situation is reversed and anions are the predominant species. The turning voltage $V_T^c$ can be defined as $$V_T^c = V_{SE}(n_{avg}^a = n_{avg}^c), \qquad (16)$$

i.e. when the average volumic concentrations for cations and anions equalize. In the case of an ideal nanopore without surface and bulk charge, the turning voltage $V_T^c$ is zero, but for a semiconductor membrane, $V_T^c$ depends on the surface charge, semiconductor doping concentration, and nanopore shape. For a surface charge of $-0.064$ C m$^{-2}$ (FIG. 11A), $V_T^c$ is around 0.25 V in our structure. FIG. 11B shows the ion concentration profiles for a membrane with a higher donor concentration, which results in a larger depletion charge, repelling cations in the pore and shifting $V_T^c$ to negative $V_{SE}$ values. However, the quantitative behavior of the concentration curves remains roughly the same, varying within similar values for the same voltage range. Therefore the cation concentration gain $\beta_c^+$ has practically the same profile as FIG. 11A inset. Changes in the surface charge do not modify qualitatively this behavior but tends to shift $V_T^c$ towards positive values as the $V_{SE}$ potential (applied to the semiconductor) is now screened by the large negative surface charge (FIG. 11C). Lowering the electrolyte concentration improves the ion selectivity of the pore: indeed, greater concentration gain $\beta_c^+$ is achieved for lower electrolyte concentrations (FIGS. 11A-D insets). This effect is due to a longer Debye length for which the double layers on each side of the nanopore overlap over the whole inner volume, while for higher electrolyte concentrations resulting in a smaller Debye length, double layer overlap occurs only in the narrowest region of the pore. One also notices that the average volumic concentration is never zero for both types of ions because of edge effects, i.e. at both extremities of the nanopore, where the influence of the voltage between the electrolyte and the semiconductor is weak and where both the anions and cations concentrations in these nanopore regions rapidly reach bulk values.

Figure 12A:
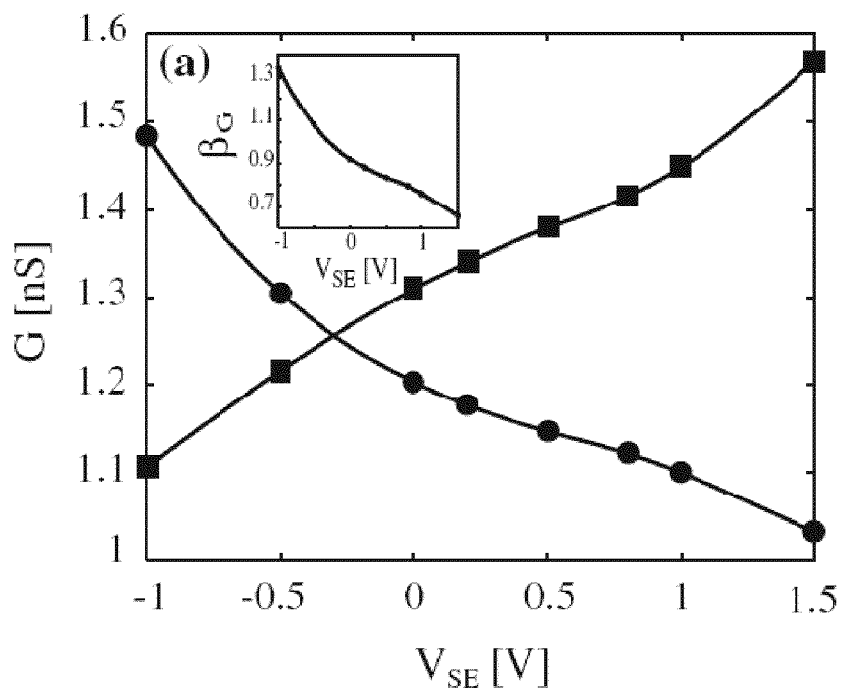
FIGS. 12A-D depict illustrative embodiments of a conductance of K$^+$ (circle) and Cl$^−$ (square) ions and insets: $β_G$ versus voltage applied.
Figure 12B:
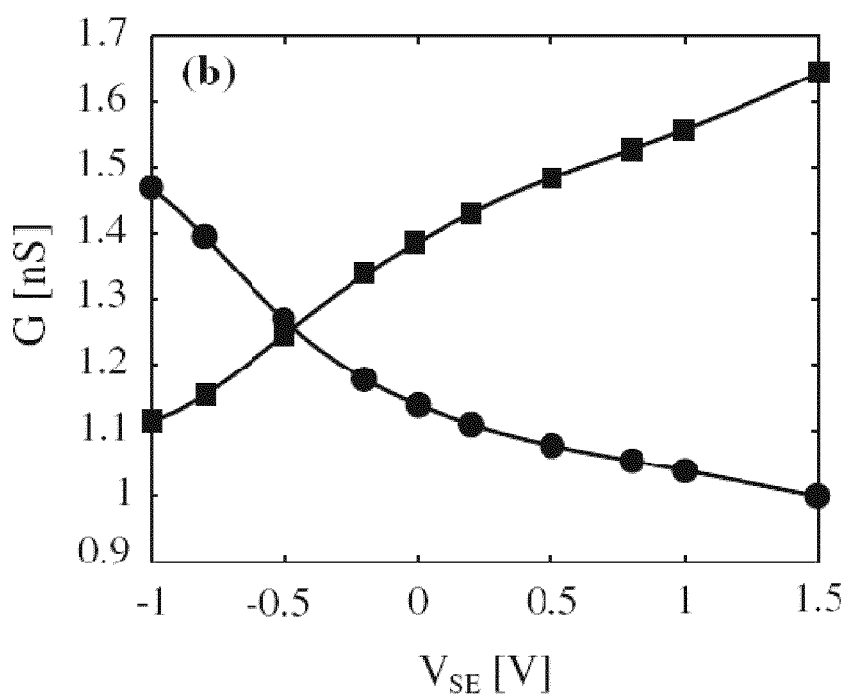

FIGS. 12A-D show the cation and anion conductance variations as a function of $V_{SE}$ for the same parameters as in FIGS. 11A-D. As for the ion concentration variations versus $V_{SE}$, we can define a conductance turning voltage $V_T^G = V_{SE}$ ($G_a = G_c$), for which the anion conductance and the cation conductance equalize. As seen in FIG. 12A, for a surface charge of $-0.064$ C m$^{-2}$, $V_T^G \approx 0.35$ V which is different from $V_T^c$ for the same conditions. This difference is mainly due to the mobility profiles which do not coincide with the ion concentration profiles inside the nanopore. Furthermore, cation bulk mobility is 10% smaller than the anion one, also resulting in a shift of $V_T^G$ towards negative voltage. High doping concentration in the n$^+$-membrane shifts $V_T^G$ towards negative values because the positive charges in the depletion layer overcomes the influence of the negative surface charge (FIG. 12B). The filter selectivity can be defined as $$S = \frac{|G_c - G_a|}{G_c + G_a} = \left|\frac{\beta_G - 1}{\beta_G + 1}\right|.$$

Figure 12C:
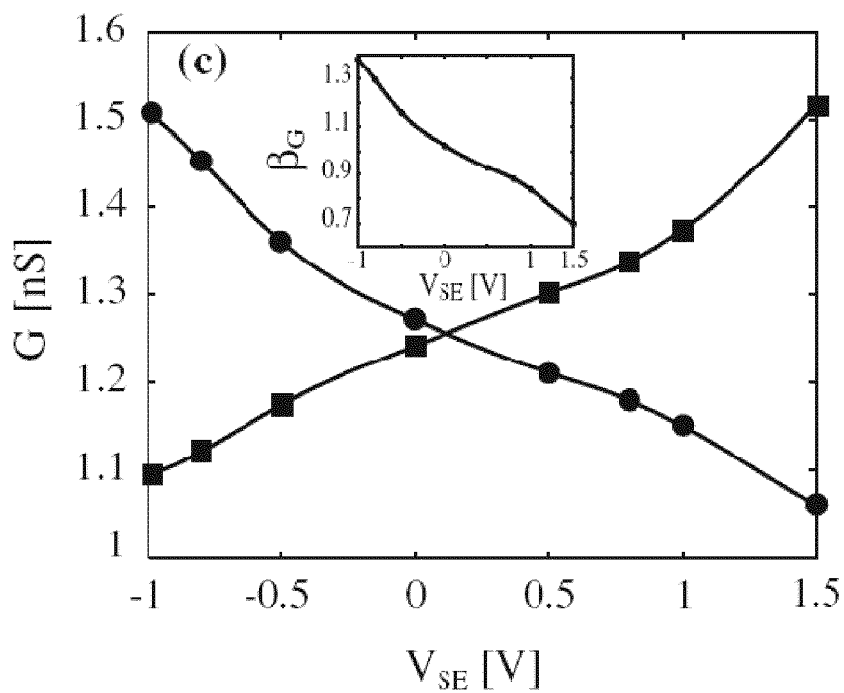
Figure 12D:
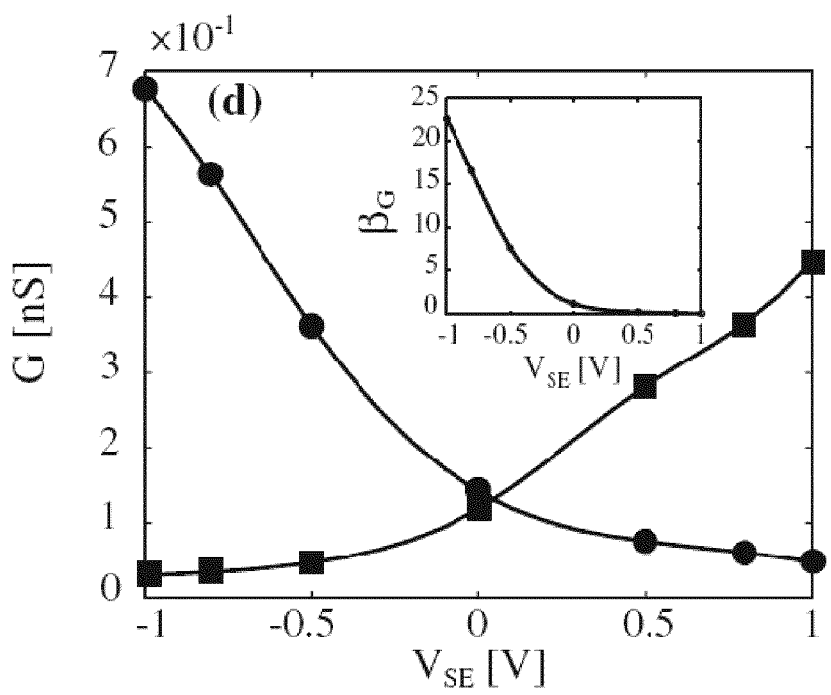

When $S \approx 1$, either $G_a$ or $G_c$ is zero, and so the nanopore allows only one type of ions to cross the membrane as in a perfect filter. If $S \approx 0$, then $G_c \approx G_a$ and the nanopore does not discriminate between both types of ions, and behaves like a passive channel between two reservoirs. For both FIGS. 12A and 12B, a conductance gain $\beta_G^+ \approx 1.3$ and a maximum selectivity $S_{max} \approx 0.15$ are achieved. Such a low efficiency can be explained by side effects at the opening regions of the pore where ions are not affected by the voltage differences applied between the semiconductor and the electrolyte and ions behave as in a bulk solution. FIG. 12C displays the conductance curves for higher surface charge ($-0.096\,\mathrm{C\,m^{-2}}$), resulting in a $V_T^G$ increase due to the negative surface charge that tends to attract more cations than anions in the nanopore. Both gain and selectivity remains the same for increasing surface charges. For a lower concentration $[K^+]_0 = [Cl^-]_0 = 0.1$ M (FIG. 12D), two phenomena arise: first the conductance for both cations and anions decreases due to the fact that less ions are present in the solution; second, greater conductance gain $\beta_G^+ \approx 23$ and a maximum selectivity $S_{max} \approx 0.92$ are achieved, due to the vanishing edge effects. Indeed, the Debye length $\lambda_D$ is now comparable to the smallest diameter in our device ($\approx 10$ Å), and then double layer overlap occurs in most of the nanopore and not only at its bottle neck. Hence, by decreasing the electrolyte concentration or the nanopore diameter of the nanopore, the selectivity of the ion filter is greatly improved.

It should be apparent to one of ordinary skill in the art from the foregoing embodiments that other suitable modifications can be applied to the present disclosure. Accordingly, the reader is directed to the claims for a fuller understanding of the breadth and scope of the present disclosure.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments, of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

References

1) Li, J.; Stein, D.; McMullan, C.; Branton, D.; Aziz, M. J.; Golovchenko, J. A. *Nature* 2001, 412, 166-169.
2) Storm, A. J.; Chen, J. H.; Ling, X. S.; Zandbergen, H. W.; Dekker, C. C. *Nat. Mater.* 2003, 2, 537-540.
3) Gracheva, M. E.; Xiong, A.; Aksimentiev, A.; Schulten, K.; Timp, G.; Leburton, J.-P. *Nanotechnology* 2006, 17, 622-633.
4) Heng, J. B.; Ho, C.; Kim, T.; Timp, R.; Aksimentiev, A.; Grinkova, Y. V.; Sligar, S.; Schulten, K.; Timp, G. *Biophys. J.* 2004, 87, 2905-2911.
5) Kasianowicz, J. J.; Brandin, E.; Branton, D.; Deamer, D. W. *Proc. Natl. Acad. Sci. U.S.A.* 1996, 93, 13770-13773.
6) Karnik, R.; Fan, R.; Yue, M.; Li, D.; Yang, P.; Majumdar, A. *NanoLett.* 2005, 5, 943-948.
7) Nishizawa, M.; Menon, V. P.; Martin, C. R. *Science* 1995, 268, 700-702.
8) Vidal, J.; Gracheva, M. E.; Leburton, J.-P. *Nanoscale Res. Lett.* 2007, 2, 61-68.
9) Ho, C.; Qiao, R.; Heng, J. B.; Chatterjee, A.; Timp, R. J.; Alum, N. R.; Timp, G. *Proc. Natl. Acad. Sci. U.S.A.* 2005, 102, 10445-10450.
10) Fologea, D.; Uplinger, J.; Thomas, B.; McNabb, D. S.; Li, J. *Nano Lett.* 2005, 5, 1734-1737.
11) Fan, R.; Karnik, R.; Yue, M.; Li, D.; Majumdar, A.; Yang, P. *Nano Lett.* 2005, 5, 1633-1637.
12) Siwy, Z.; Heins, E.; Harrell, C.; Kohli, P.; Martin, C. *J. Am. Chem. Soc.* 2004, 126, 10850-10851.
13) Horiuchi, P.; Dutta, P. *Lab Chip* 2006, 6, 714-723.
14) Daiguji, H.; Oka, Y.; Shirono, K. *Nano Lett.* 2005, 5, 2274-2280.
15) Gracheva, M. E.; Leburton, J.-P. *Nanotechnology* 2007, 18, 145704-145710.
16) Dimitrov, V.; Aksimentiev, A.; Schulten, K.; Heng, J.; Sorsch, T.; Mansfield, W.; Miner, J.; Watson, G. P.; Cirelli, R.; Klemens, F.; Bower, J.; Ferry, E.; Taylor, A.; Komblit, A.; Dorvel, B.; Zhao, Q.; limp, G. Exploring the Prospects for a Nanometer-Scale Gene Chip. In *IEDM Tech. Digest* 2006, 169-173.
17) Gardner, C. L.; Nonner, W.; Eisenberg, R. S. *J. Comput. Electron.* 2004, 3, 25-31.
18) Ramîrez, P.; Mafé, S.; Aguilella, V. M.; Alcaraz, A. *Phys. ReV. E* 2003, 68, 011910(1)-011910(8).
19) Siwy, Z. *AdV. Funct. Mater.* 2006, 16, 735-746.
20) Vlassiouk, I.; Siwy, Z. S, *Nano Lett.* 2007, 7, 552-556.
21) Karnik, R.; Duan, C.; Castelino, K.; Daiguji, H.; Majumdar, A. *Nano Lett.* 2007, 7, 547-551.
22) D. A. Doyle, J. M. Cabral, R. A. Ofuetzner, A. Kuo, J. M. Gulbis, S. L. Cohen, B. T. Chait, R. MacKinnon, Science 280, 69 (1998)
23) J. Li, M. Gershow, D. Stein, E. Brandin, J. A. Golovchenko, Nat Mater 2, 611 (2003)

24) H. Li, Y. Zheng, D. Akin, R. Bashir, J. Microelectromech. Syst. 14, 103 (2005)
25) J. G. Kralj, M. T. W. Lis, M. A. Schmidt, K. F. Jensen, Anal. Chem. 78, 5019 (2006)
26) D. Stein, J. Li, J. A. Golovchenko, Phys. Rev. Lett. 89, 276106 (2002)
27) J. D. Zhou, S. T. Cui, H. D. Cochran, Mol. Phys. 101a, 1089 (2003)
28) J. B. Heng, A. Aksimentiev, C. Ho, P. Marks, V. V. Grinkova, S. Sligar, K. Schulten, G. Timp, Biophys. J. 90, 1098 (2006)

What is claimed is:

1. A solid-state selector, comprising:
   a vessel for carrying a liquid medium;
   a solid state conductive structure having one or more through-holes, wherein the solid state conductive structure has first and second layers, wherein the first layer is doped with a p-type impurity, and wherein the second layer is doped with a n-type impurity;
   a first voltage source coupled to the first layer; and
   a second voltage source coupled to the second layer, wherein the first and second voltage sources selectively stimulates particles in the liquid medium through the one or more through-holes.

2. The solid-state selector of claim 1, wherein the liquid medium comprises one or more molecules surrounded by ions.

3. The solid-state selector of claim 2, wherein the first and second voltage sources selectively stimulate at least one of the ions, the one or more molecules, or both to control a flow of the one or more molecules through the one or more through-holes.

4. The solid-state selector of claim 1, wherein each of the one or more through-holes have an opening of less than 30 nanometers.

5. The solid-state selector of claim 1, wherein each of the one or more through-holes has a double conical shape.

6. The solid-state selector of claim 1, wherein the liquid medium comprises an electrolyte, and wherein the solid-state selector comprises first and second electrodes disposed in the electrolyte to control ionic current.

7. The solid-state selector of claim 2, wherein the ions comprise cations and anions.

8. The solid-state selector of claim 7, wherein one or more voltages applied by at least one of the first voltage source, the second voltage source, or both causes an inverse relation between a concentration of the anions and the cations passing through the one or more through-holes.

9. The solid-state selector of claim 7, wherein one or more voltages applied by at least one of the first voltage source, the second voltage source, or both causes an equal concentration of the anions and the cations passing through the one or more through-holes.

10. The solid-state selector of claim 7, wherein one or more voltages applied by at least one of the first voltage source, the second voltage source, or both stimulates the anions to pass through the one or more through-holes and repels the cations from passing through the one or more through-holes.

11. The solid-state selector of claim 7, wherein one or more voltages applied by at least one of the first voltage source, the second voltage source, or both stimulates the cations to pass through the one or more through-holes and repels the anions from passing through the one or more through-holes.

12. The solid-state selector of claim 1, wherein the one or more through-holes each comprise one of a slit or a pore.

13. The solid-state selector of claim 1, comprising a transport event pulse detector having at least one conductor coupled to the solid state conductive structure for detecting a sequence of transport event pulses responsive to a particle traversing the one or more through-holes, and wherein said sequence of transport event pulses defines in whole or in part are descriptive of a chemical composition.

14. The solid-state selector of claim 1, wherein the solid state selector is at least one of an ion filter, a molecular filter, or a genetic sensor.

15. A solid-state device, comprising:
    a vessel for carrying a liquid medium;
    a solid state conductive structure having one or more through-holes extending between first and second layers of the solid state conductive structure, wherein the first layer is doped with a first impurity, and wherein the second layer is doped with a second impurity, and wherein the first and second impurities differ in their conductivity;
    a first voltage source coupled to the first layer of the solid state conductive structure; and
    a second voltage source coupled to the second layer of the solid state conductive structure, wherein the first and second voltage sources selectively control a flow of particles in the liquid medium in a vicinity of the one or more through-holes.

16. The solid-state device of claim 15, wherein the particles comprise one or more molecules surrounded by ions.

17. The solid-state device of claim 16, wherein the first and second voltage sources selectively stimulate at least one of the ions, the one or more molecules, or both to control a flow of the one or more molecules through the one or more through-holes.

* * * * *